(12) United States Patent
Adler, Jr. et al.

(10) Patent No.: US 9,271,673 B2
(45) Date of Patent: Mar. 1, 2016

(54) NIR IMAGE-GUIDED TARGETING

(71) Applicant: Varian Medical Systems, Inc., Palo Alto, CA (US)

(72) Inventors: John R. Adler, Jr., Stanford, CA (US); Agam Sharda, Fremont, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 140 days.

(21) Appl. No.: 14/040,604

(22) Filed: Oct. 2, 2013

(65) Prior Publication Data

US 2014/0121494 A1 May 1, 2014

Related U.S. Application Data

(60) Provisional application No. 61/719,301, filed on Oct. 26, 2012, provisional application No. 61/798,066, filed on Mar. 15, 2013.

(51) Int. Cl.

| A61B 5/00 | (2006.01) |
| A61B 5/055 | (2006.01) |
| A61B 6/03 | (2006.01) |
| A61N 5/10 | (2006.01) |
| A61N 5/06 | (2006.01) |

(52) U.S. Cl.
CPC .............. *A61B 5/4836* (2013.01); *A61B 5/0035* (2013.01); *A61B 5/0071* (2013.01); *A61B 5/0075* (2013.01); *A61B 5/055* (2013.01); *A61B 5/441* (2013.01); *A61B 5/0064* (2013.01); *A61B 6/032* (2013.01); *A61N 5/1049* (2013.01); *A61N 2005/0626* (2013.01)

(58) Field of Classification Search
CPC .. A61B 5/4836; A61B 5/0035; A61B 5/0071; A61B 5/0075; A61B 5/055; A61B 5/441; A61B 5/4887; A61B 5/72; A61B 5/4504; A61B 5/0064; A61B 6/032; A61B 5/1049; A61N 2005/0626
See application file for complete search history.

(56) References Cited

U.S. PATENT DOCUMENTS

| 7,505,559 | B2* | 3/2009 | Kuduvalli | ............ | A61N 5/1049 378/205 |
| 7,720,196 | B2* | 5/2010 | Zhang | ............ | A61B 5/113 378/65 |
| 8,235,530 | B2* | 8/2012 | Maad | ............ | A61B 6/0407 250/492.1 |
| 2003/0018271 | A1* | 1/2003 | Kimble | ............ | A61B 5/0059 600/473 |
| 2013/0006036 | A1* | 1/2013 | Raleigh | ............ | A61N 5/1049 600/1 |

* cited by examiner

*Primary Examiner* — Long V Le
*Assistant Examiner* — Colin T Sakamoto

(57) ABSTRACT

A method for targeting. The method includes determining skin characteristics in a region of a patient. An in-treatment optical scan is performed on a region of a patient, wherein the in-treatment optical scan comprises a near infrared (NIR) energy source. A plurality of detected signals is detected from the optical scan. The skin characteristics are filtered out from the plurality of detected signals. Skeletal anatomy positioning associated with the region is determined from the plurality of signals that is filtered.

8 Claims, 6 Drawing Sheets

NIR IMAGE-GUIDED TARGETING

CROSS REFERENCE TO RELATED APPLICATIONS

This application claims priority to and the benefit under 35 U.S.C §119(e) of U.S. Provisional Patent Application No. 61/719,301, filed on Oct. 26, 2012, entitled "NIR IMAGE GUIDED TARGETING," the disclosure of which is hereby incorporated by reference in its entirety. This application also claims priority to and the benefit under 35 U.S.C §119(e) of U.S. Provisional Patent Application No. 61/798,066, filed Mar. 15, 2013, entitled "APPARATUS AND METHOD FOR REAL-TIME TRACKING OF BONY STRUCTURES," the disclosure of which is hereby incorporated by reference in its entirety.

This application is related to U.S. patent application Ser. No. 14/040,609, filed on Sep. 27, 2013, entitled APPARATUS AND METHOD FOR REAL-TIME TRACKING OF BONY STRUCTURES, the disclosure of which is hereby incorporated by reference in its entirety.

BACKGROUND

Image-guided targeting has a growing role in a range of medical procedures. At its foundation, image-guidance involves the computer correlation of near real time imagery with an historic three-dimensional (3D) volumetric data to determine the spatial location of patient anatomy. That is, image-guided targeting includes techniques and processes that are used to create images of the human body. Typical examples of 3D volumetric data for image-guided targeting include computed tomography (CT) or magnetic resonance imaging (MRI).

The use of this image-guided targeting has been best described for precise localization of patient bony anatomy in 3D space using projection x-rays or cone beam CT. The tacit assumption that underlies most image-guidance is that skeletal anatomy can provide a reliable reference for nearby soft tissue. Sub-millimetric targeting accuracy is possible with such techniques, thereby enabling even the most precise surgical procedures to be performed under image-guidance.

The primary role of x-rays in image-guidance is to define the 3D location of bony anatomy for image-correlation. Their relative capacity to penetrate skin is the cardinal feature of x-rays that enables them to be used for imaging. In contrast, the kilovoltage energy x-rays used in image-guidance are characterized by a much greater proclivity to be scattered off bone, and therefore a much greater likelihood of being blocked from transmission through the tissue being imaged.

Although imaging with x-rays is robust, the challenge of using ionizing radiation burdens this approach because ionizing x-rays are potentially harmful to patients and the medical team. As such, current technologies using ionizing x-rays for image-guidance is rarely done on a continuous basis. For example cone beam CT scans are generally only produced at the start of a several minute to several hour procedure, while projection x-rays used for image correlation are only generated every 20 to 60 sec. The infrequency of such "real time" imaging means that instantaneous patient movement goes undetected, and will result in therapeutic inaccuracies.

What is needed is a truly real time imaging modality that can be correlated to 3D patient anatomy.

SUMMARY

A method for treatment of a patient is disclosed. The method includes determining skin characteristics in a region of a patient. The method includes performing an in-treatment optical scan on a region of the patient, wherein the in-treatment optical scan comprises a near infrared (NIR) energy source. The method includes detecting a plurality of detected signals from the optical scan. The method includes filtering out the skin characteristics from the plurality of detected signals. The method includes determining skeletal anatomy associated with the region from the plurality of signals that is filtered.

In another embodiment, another method for treatment is disclosed. The method includes performing a base scan to obtain relative 3D (three dimensional) positioning of a target within a skeletal anatomy of a patient. The method also includes performing an in-treatment optical scan on the patient to determine 3D positioning of the skeletal anatomy within a treatment system, wherein the in-treatment optical scan comprises a near infrared (NIR) energy source. Further, the operation of performing an in-treatment optical scan includes detecting a plurality of detected signals from the optical scan, and filtering out signaling characteristics for skin of the patient from the plurality of detected signals to obtain signals related to the skeletal anatomy and determine the 3D positioning of the skeletal anatomy. The method also includes registering the 3D positioning of the skeletal anatomy from the in-treatment optical scan and the 3D positioning of the skeletal anatomy determined from the base scan to determine relative positioning of the target within the treatment system.

In another embodiment, a system for providing treatment is disclosed. The system includes a skin detector for determining skin characteristics in a region of a patient. The system also includes an in-treatment near infrared (NIR) optical scanner for performing an in-treatment optical scan on a region of the patient, wherein the in-treatment optical scan comprises a near infrared (NIR) energy source. The system includes at least one detector for detecting a plurality of detected signals from the optical scan. The system includes a filter for filtering out the skin characteristics from the plurality of detected signals. The system also includes a modeling module for determining skeletal anatomy associated with the region from the plurality of signals that is filtered.

BRIEF DESCRIPTION

The accompanying drawings, which are incorporated in and form a part of this specification and in which like numerals depict like elements, illustrate embodiments of the present disclosure and, together with the description, serve to explain the principles of the disclosure.

DETAILED DESCRIPTION

Figure 1:
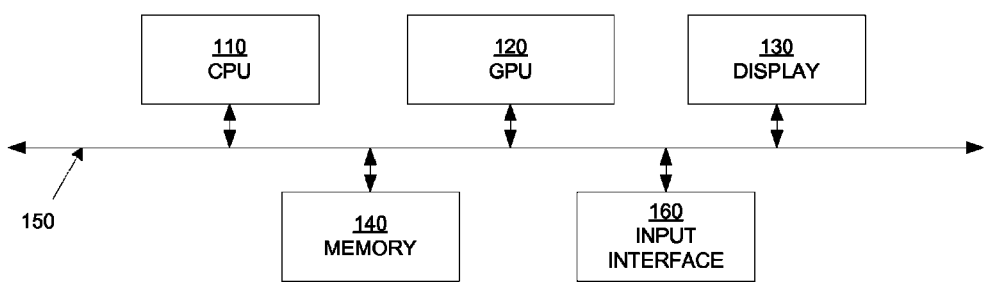
FIG. 1 depicts a block diagram of an exemplary computer system suitable for implementing the present methods, in accordance with one embodiment of the present disclosure.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "performing," "varying," "filtering," "detecting," "determining," or the like, refer to actions and processes of a computer system or similar electronic computing device or processor. The computer system or similar electronic computing device manipulates and transforms data represented as physical (electronic) quantities within the computer system memories, registers or other such information storage, transmission or display devices.

Flowcharts are provided of examples of computer-implemented methods for processing data according to embodiments of the present invention. Although specific steps are disclosed in the flowcharts, such steps are exemplary. That is, embodiments of the present invention are well-suited to performing various other steps or variations of the steps recited in the flowcharts.

Embodiments of the present invention described herein are discussed within the context of hardware-based components configured for monitoring and executing instructions. That is, embodiments of the present invention are implemented within hardware devices of a micro-architecture, and are configured for monitoring for critical stall conditions and performing appropriate clock-gating for purposes of power management.

Other embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 is a block diagram of an example of a computing system 100 capable of implementing embodiments of the present disclosure. Computing system 100 broadly represents any single or multi-processor computing device or system capable of executing computer-readable instructions. Examples of computing system 100 include, without limitation, workstations, laptops, client-side terminals, servers, distributed computing systems, handheld devices, or any other computing system or device. In its most basic configuration, computing system 100 may include at least one processor 110 and a system memory 140.

Both the central processing unit (CPU) 110 and the graphics processing unit (GPU) 120 are coupled to memory 140. System memory 140 generally represents any type or form of volatile or non-volatile storage device or medium capable of storing data and/or other computer-readable instructions. Examples of system memory 140 include, without limitation, RAM, ROM, flash memory, or any other suitable memory device. In the example of FIG. 1, memory 140 is a shared memory, whereby the memory stores instructions and data for both the CPU 110 and the GPU 120. Alternatively, there may be separate memories dedicated to the CPU 110 and the GPU 120, respectively. The memory can include a frame buffer for storing pixel data drives a display screen 130.

The system 100 includes a user interface 160 that, in one implementation, includes an on-screen cursor control device.

The user interface may include a keyboard, a mouse, and/or a touch screen device (a touchpad).

CPU 110 and/or GPU 120 generally represent any type or form of processing unit capable of processing data or interpreting and executing instructions. In certain embodiments, processors 110 and/or 120 may receive instructions from a software application or hardware module. These instructions may cause processors 110 and/or 120 to perform the functions of one or more of the example embodiments described and/or illustrated herein. For example, processors 110 and/or 120 may perform and/or be a means for performing, either alone or in combination with other elements, one or more of the monitoring, determining, gating, and detecting, or the like described herein. Processors 110 and/or 120 may also perform and/or be a means for performing any other steps, methods, or processes described and/or illustrated herein.

In some embodiments, the computer-readable medium containing a computer program may be loaded into computing system 100. All or a portion of the computer program stored on the computer-readable medium may then be stored in system memory 140 and/or various portions of storage devices. When executed by processors 110 and/or 120, a computer program loaded into computing system 100 may cause processor 110 and/or 120 to perform and/or be a means for performing the functions of the example embodiments described and/or illustrated herein. Additionally or alternatively, the example embodiments described and/or illustrated herein may be implemented in firmware and/or hardware.

In embodiments of the present invention, near infrared light is used for image-guided targeting. Near infrared (NIR) energy (e.g., light) is defined as a spectrum of electromagnetic energy ranging from about 740 nm to 1000 nm. At these energies, photons have some capacity to pass through modest amount of tissue before being completely scattered. Different tissues result in a range of scattering patterns, with one being opaque to NIR penetration. In this sense, NIR has common scattering properties with ionizing x-rays. Embodiments of the present invention use these properties to localize in 3D space the position of the skeletal anatomy, thereby obviating the need for x-rays.

Other embodiments of the present invention provide for skin characterization, 3D localization of skeletal anatomy of an object and/or patient, and 3D localization of soft tissue targets of an object and/or patient. In particular, in one embodiment, the use of a high energy, collimated laser or similar light source (e.g., NIR, etc.) is used to characterize a patient's skin characteristics. The energy source is of sufficient strength to penetrate but not to harm the patient. In another embodiment, the use of NIR is used to visualize the patient's skeletal anatomy using IR reflectance and mapping.

Figure 2A:
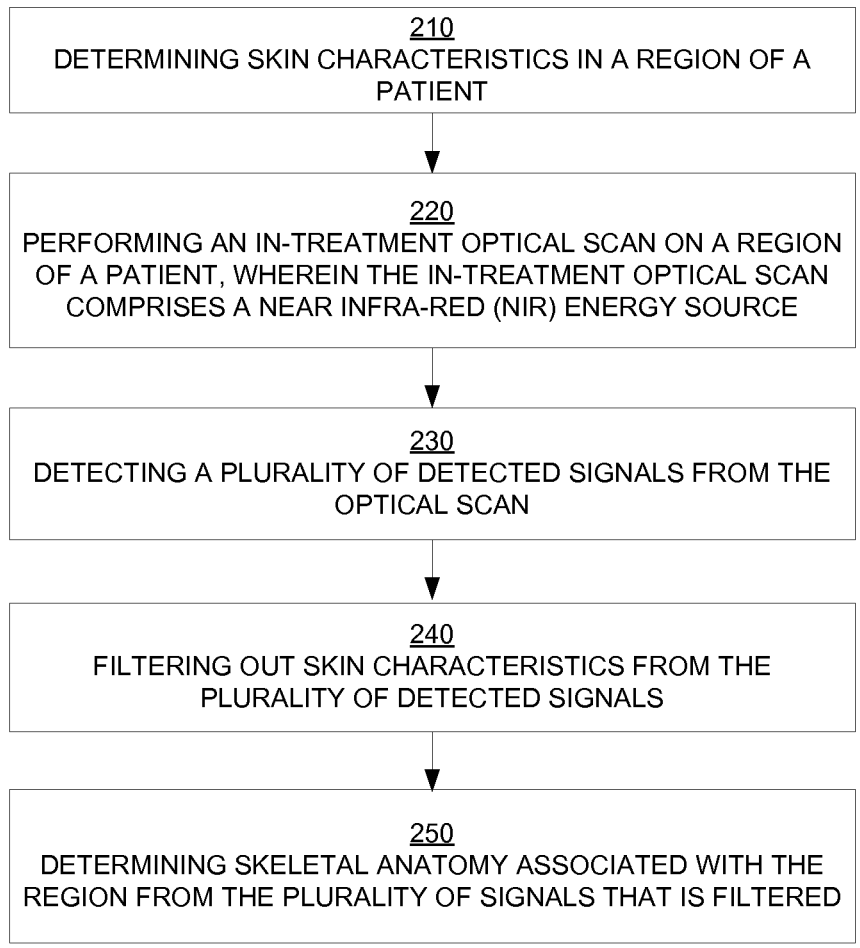
FIG. 2A is a flow diagram 200A illustrating a process for determining skeletal anatomy information of a patient using NIR imaging data, in accordance with one embodiment of the present disclosure.

FIG. 2A is a flow diagram 200A illustrating a process for determining skeletal anatomy information of a patient using NIR imaging data, in accordance with one embodiment of the present disclosure. Some or all of the operations in flow diagram 200A are performed within a computer system including a processor and memory coupled to the processor and having stored therein instructions that, if executed by the computer system cause the system to execute a method for determining skeletal anatomy information of a patient using NIR imaging data. In still another embodiment, instructions for performing a method are stored on a non-transitory computer-readable storage medium having computer-executable instructions for causing a computer system to perform a method for determining skeletal anatomy information of a patient using NIR imaging data. The method outlined in flow diagram 200A is implementable by one or more of the components of the computer system 100 and systems 300A and 300B of FIGS. 3A and 3B, respectively.

At 210, the method includes determining skin characteristics of an object or patient. More specifically, the skin characteristics are determined for a region of a patient. For instance, skin characteristics are determined for a skull region. In other examples, skin characteristics are determined for a region located on a torso of the patient. The region is generally near a surgical target located on or within the patient.

In one embodiment, the skin characteristics are determined by performing an NIR optical scan. For instance, in one embodiment, the use of NIR for the imaging and mapping of a patient's skeletal anatomy involves the characterization of the amount of signal that is absorbed by the patient's skin. This is achieved by using a high intensity laser with a known wavelength and intensity. As such, the use of NIR or other suitable signaling allows for a means of characterizing a patient's external skin characteristics. Also, the use of NIR allows for the means to illuminate the skeletal anatomy in real-time.

For example, when determining skin characteristics, the method includes performing another optical scan on the region of the patient using another source emitting NIR energy. In one embodiment, the source emits energy of varying intensity for a given frequency. In another embodiment the source emits energy of varying frequency. In still another embodiment, the source emits energy of varying intensity and frequency (e.g., wavelength). The method further includes determining signaling characteristics for skin related to at least one of skin reflectance characteristics, skin transmittive characteristics, and a skin fluorescence characteristics, such that the signaling characteristics are filterable from the plurality of detected signals. As such, in one embodiment, the data collected provides a reflectance "spectral cube" which could be assessed for maximal reflectance of underlying anatomy (e.g., through filtering).

In still another embodiment, a higher energy NIR source could be used to elicit excitation of skeletal anatomy and collection of the reflectance signal directly for determining skeletal information (e.g., positioning), in another embodiment. Specifically, the method includes performing another optical scan on the patient across varying frequencies and intensity using another NIR energy source. An optimal frequency and intensity combination is determined that optimally illuminates the skeletal anatomy with minimal skin signaling characteristics. As such, the skin characteristics need not be filtered, and as such, the in-treatment optical scan is performed on the patient using the optimal frequency and intensity combination, such that filtering of the skin characteristics are unnecessary.

In another embodiment, the skin characteristics are determined using traditional methods, such as, those performed with using computed tomography (CT) or magnetic resonance imaging (MRI). While true characterization of an individual patient's skin can be carried out by extracting a histological sample of the tissue, it is obviously not conducive for real world clinical treatments in radiation therapy. As such, embodiments of the present invention provide for non-invasive spectroscopic methods to perform skin characterization, to include the following techniques, such as, diffuse reflectance, fluorescence, X-ray fluorescence (XRF) Fourier Transform IR (FTIR), among others.

At 220, the method includes performing an in-treatment optical scan on a region of the patient. The optical scan is performed using an NIR energy source or optical scanner. For example, post skin characterization, in situ visualization of the skeletal anatomy is performed using a broadband, NIR source, and appropriate sensor, as will be described in relation to FIGS. 3B and 3C. The in-treatment optical scan process includes detecting a plurality of detected signals from the optical scan at 230. For instance, the detectors are configurable to receive signals that re reflected off the patient, transmittive signals that are transmitted through the patient, and fluorescence signals that are emitted from the patient.

Additionally, at 240, the method includes filtering out skin characteristics for the plurality of detected signals. That is, the data collected at the plurality of detectors is then filtered to remove the contribution from the individual patient's skin that is derived from the characterization step performed at 210. For instance, these calculations can all be carried out on a commercially available GPU based processor providing the capability of real time visualization of skeletal anatomy.

At 250, the method includes determining skeletal anatomy information associated with the region from the plurality of signals that is filtered. In particular, skin characterization increases the accuracy of radiation treatment. That is, the plurality of detected signals can be de-convoluted to remove the contribution from the skin. As such, the underlying skeletal anatomy is obtained.

Figure 2B:
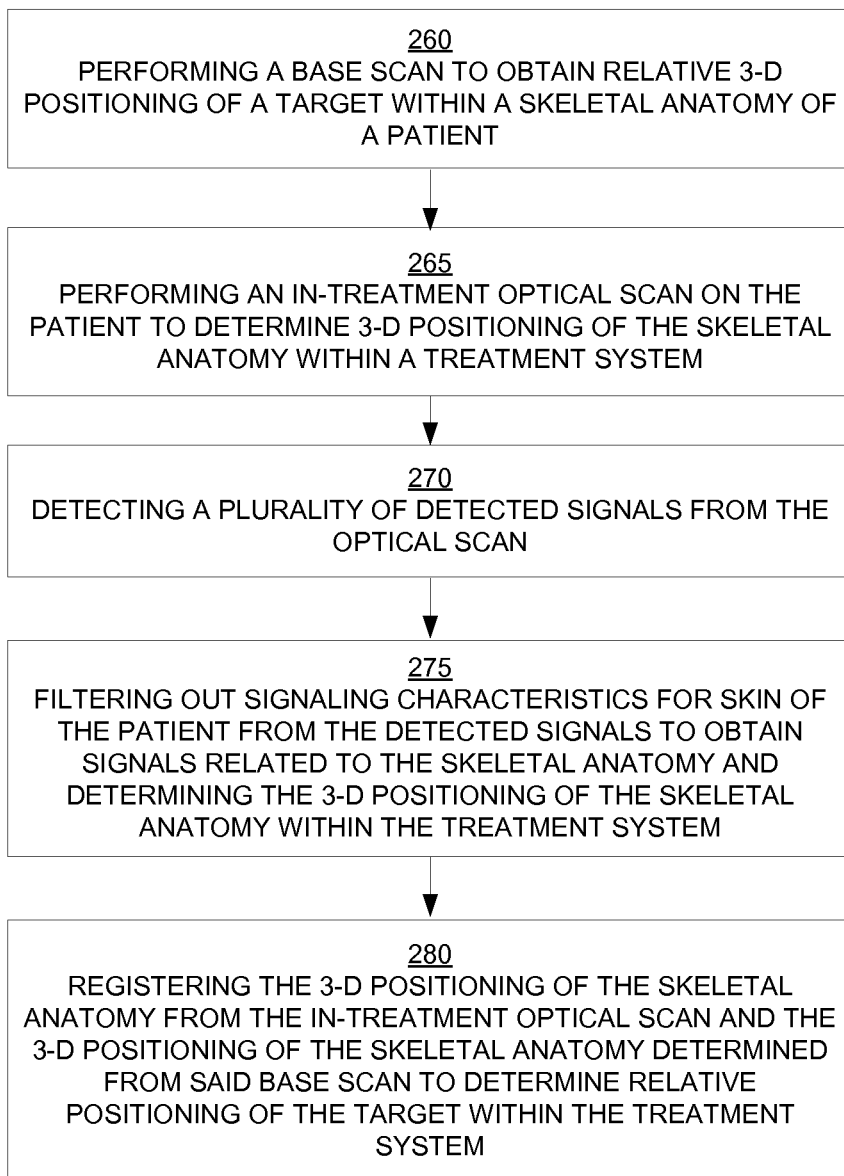
FIG. 2B is a flow diagram 200B illustrating a process for localizing the skeletal anatomy of an object or patient using NIR imaging data, in accordance with one embodiment of the present disclosure.

FIG. 2B is a flow diagram 200B illustrating a process for localizing the skeletal anatomy of an object or patient using NIR imaging data, in accordance with one embodiment of the present disclosure. Some or all of the operations in flow diagram 200B are performed within a computer system including a processor and memory coupled to the processor and having stored therein instructions that, if executed by the computer system cause the system to execute a method for localizing the skeletal anatomy of an object or patient using NIR imaging data. In still another embodiment, instructions for performing a method are stored on a non-transitory computer-readable storage medium having computer-executable instructions for causing a computer system to perform a method for localizing the skeletal anatomy of an object or patient using NIR imaging data. The method outlined in flow diagram 200B is implementable by one or more of the components of the computer system 100 and systems 300A and 300B of FIGS. 3A and 3B, respectively.

At 260, the method includes performing a base scan to obtain relative 3D positioning of a surgical target within a skeletal anatomy of an object or patient. For instance, the base scan includes traditional methodology for performing a planning CT, or MRI. The information obtained from the base scan includes, in part skin characterization information, and skeletal anatomy information.

At 265, the method includes performing an in-treatment optical scan on the patient to determine 3D positioning of the skeletal anatomy within a treatment system or environment. For instance, the method includes illuminating a patient's anatomy with a high intensity NIR source.

At 270, the method includes detecting a plurality of detected signals derived from the optical scan. For instance, the method includes measuring or detecting transmitted, reflected, and fluorescent energy with one or more precisely calibrated sensors/cameras.

At 275, the method includes filtering out signaling characteristics for skin of the patient from the plurality of detected signals to obtain signals related to the skeletal anatomy. In that manner, the 3D positioning of the skeletal anatomy within the treatment system can also be determined. For instance, the method includes using intensity of light and time of flight analysis of the recorded and filtered signal to triangulate and deduce the precise 3D spatial location of the object (e.g., skeletal) surface.

At 280, the method includes co-registering the skeletal model to the reference patient CT or MRI dataset for purposes of accurate patient positioning. Specifically, the method includes registering the 3D positioning of the skeletal anatomy obtained from the in-treatment optical scan and the 3D positioning of the skeletal anatomy determined from the base scan to determine relative positioning of the surgical target within the treatment system. That is, image-to-image correlation is performed, such that the image of the skeletal anatomy is correlated with a prior scan (e.g., CT, MT, or MRI) scan generated through the same object or patient anatomy. The 3D images of the skeletal anatomy scans are compared to determine a closest fit of data. For instance, a least squared comparison process will find the closest fit between the NIR image of anatomy and the previously obtained CT/MRI volumetric data. Thereafter, extrapolation may be performed to determine the 3D spatial location of the surgical target within the object and/or patient. As such, the 3D spatial location of the surgical target is obtained within the treatment system through extrapolation.

Once localization of the patient within the treatment system is known, the method includes broadly positioning skeletal and/or human anatomy such that radiation is properly directed to the surgical target. More specifically, after localization of the patient, if it is found that the surgical target is misaligned with treatment beam radiation, an adjustment is made to the relative positioning between human anatomy and the treatment beam radiation is performed. In that manner, proper alignment of the surgical target with the treatment beam radiation is achieved.

More specifically, once the location of the surgical target is known in relation to the skeletal anatomy, precisely calibrated cameras and appropriate software can then be used to guide stereotactic procedures. That is, the surgical target is then exposed to the treatment beam radiation from the treatment system. Because no ionizing radiation is being used during the localization process, the process of determining skeletal and therefore target position can be continuous, in embodiments of the present invention. That is, the in-treatment optical scan can be performed on the patient on a periodic basis under various medical applications to provide consistent and accurate positioning of patients in relation to the treatment system (e.g., treatment beam radiation) during diagnostic imaging and the positioning of invasive or minimally invasive surgical tools. In one embodiment, the scans are performed 1-5 times per second. In another embodiment, the scans are performed between 20-30 scans per second. Even higher rates are achievable, in other embodiments. In summary, the base scan provides localization of the surgical target within the skeletal anatomy. The in-treatment optical scan provides location of the skeletal anatomy within the treatment system. By registering the skeletal anatomy derived from the base scan with the skeletal anatomy derived from the in-treatment optical scan, localization of the surgical target within the treatment system is obtained. In that manner, accurate positioning of the patient is achieved for proper treatment.

As a result, with continuous patient localization, the method includes updating registration of the 3D positioning of said skeletal anatomy obtained from the in-treatment optical scan and the 3D positioning of the skeletal anatomy determined from the base scan based on a current in-treatment optical scan to determine current relative positioning of the surgical target within the treatment system. As such, the method also includes aligning the target and the treatment beam radiation based on the current relative positioning to expose the target to the treatment beam radiation.

In still other embodiments, the broad positioning of the patient is performed within the context of any diagnostic system or any automated system requiring accurate positioning of the patient within that system, and possibly wherein no ionizing radiation is used for treatment. For instance, the patient may be undergoing a routine diagnostic MRI, CT or PET scan, such as, those used for planning. As such, once the location of the patient or a region of the patient is known within the diagnostic system, the relative positioning of the patient and the diagnostic system may be adjusted to improve diagnostic testing. For example, the patient may be repositioned within the diagnostic system. That is, the patient may be repositioned within the MRI, CT, or PET scanning apparatus with the aid of the NIR positioning device that uses NIR imaging to determine localization of the patient within the diagnostic system. In other applications, the patient may be undergoing a surgical operation with the use of systems for performing automated surgical techniques or guidance systems used for aiding a surgeon during the operation (e.g., guiding the placement of a knife when making an incision on a surgical target). As such, the NIR positioning device using NIR imaging is used to properly position and align the patient within the system for accurate treatment. Also, the NIR positioning device is used to provide guidance during a surgical procedure by properly positioning the surgical target within the surgical environment, identifying the surgical target, and verifying the proper location of the surgical target, such that the information may be used to help guide the hand of the surgeon during the surgical procedure.

The accuracy and sensitivity of the various approaches presented in embodiments of the present invention rely may rely on the strength of the reflectance signal received from the skeletal anatomy of interest and on the sensitivity of the detection sensor. In one embodiment, it is advantageous to use a sensor with high spectral and spatial resolution in the NIR spectrum.

Figure 3A:
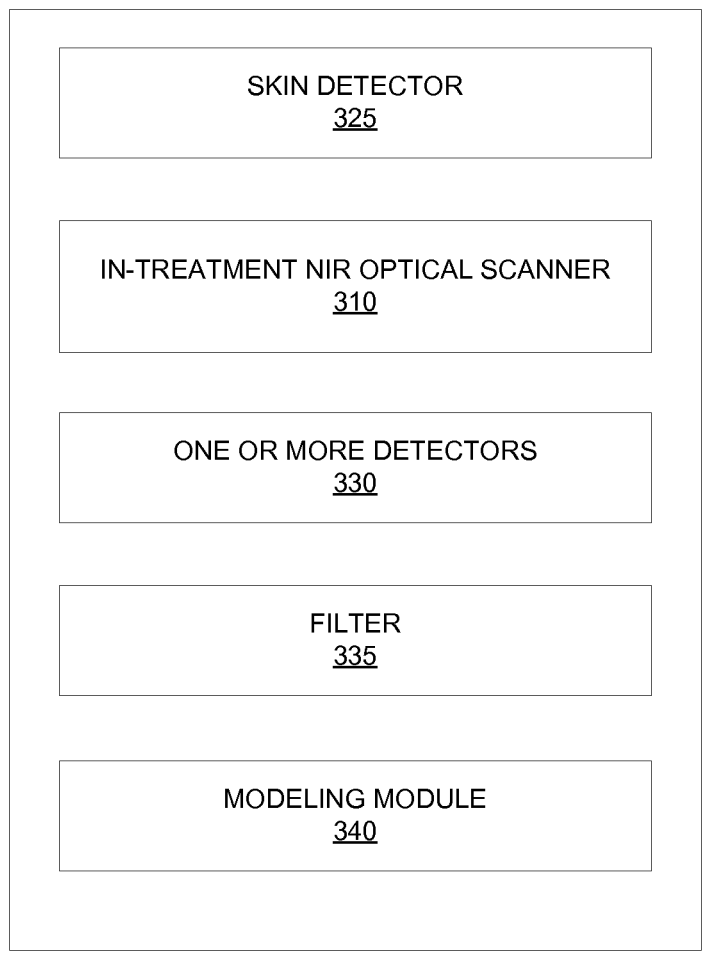
FIG. 3A is a block diagram of a treatment system configured for performing 3D patient modeling through NIR imaging, in accordance with one embodiment of the present disclosure.

FIG. 3A is a block diagram of a treatment system 300A configured for performing 3D patient modeling through NIR imaging, in accordance with one embodiment of the present disclosure. For instance, treatment system 300A is configurable to implement the method of FIG. 2A, and portions of FIG. 2B to provide real-time patient modeling and localization during an in-treatment procedure, in one embodiment. That is, the treatment system 300A is implementable to provide patient modeling and localization in order to provide accurate beam placement on a surgical target within a skeletal anatomy of a patient.

Treatment system 300A includes a skin detector 325 configured for determining skin characteristics of a patient. As previously described, the skin detector may include a traditional CT, MT, or MRI scanning system to determine skin characteristics. In another embodiment, the skin detector 325 may include an NIR optical scanner used to determine customized data related to skin characteristics of a particular patient. For example, signaling related to the skin characteristics may be determinable, and later filtered out to obtain signaling information related to the skeletal anatomy, when the patient is illuminated with NIR energy. For instance, skin detector 325 may perform operation 210 in FIG. 2A, and operation 260 in FIG. 2B, in embodiments.

Treatment system 300A also includes an in-treatment NIR optical scanner 310 configured for performing an in-treatment optical scan on a region of the patient. Information obtained from the optical scanner 310 is used to determine 3D positioning of the skeletal anatomy within a treatment system. For instance, the NIR optical scanner 310 is used to perform operation 220 of FIG. 2A, and 265 of FIG. 2B.

Treatment system 300A also includes one or more detectors 330 configured for measuring and/or detecting one or more of reflected signals, transmitted signals, or fluorescent signals excited and/or derived from the NIR optical scanner 310 after interaction with the patient. For instance, detector 330 is configured to perform operations 230 of FIG. 2A, and 270 of FIG. 2B. Treatment system 300A also includes a filter 335 for filtering out skin characteristics from the plurality of detected signals. For instance, filter 335 is configured to perform operations 240 of FIG. 2A, and 275 of FIG. 2B.

Treatment system 300A also includes a modeling module 340 configured for determining skeletal anatomy of the patient from the filtered and detected signals. In particular, the modeling module 340 models a region of the patient, wherein the region is near to the surgical target. As such, a model of the skeletal anatomy in the region is created by the modeling module 340.

Figure 3B:
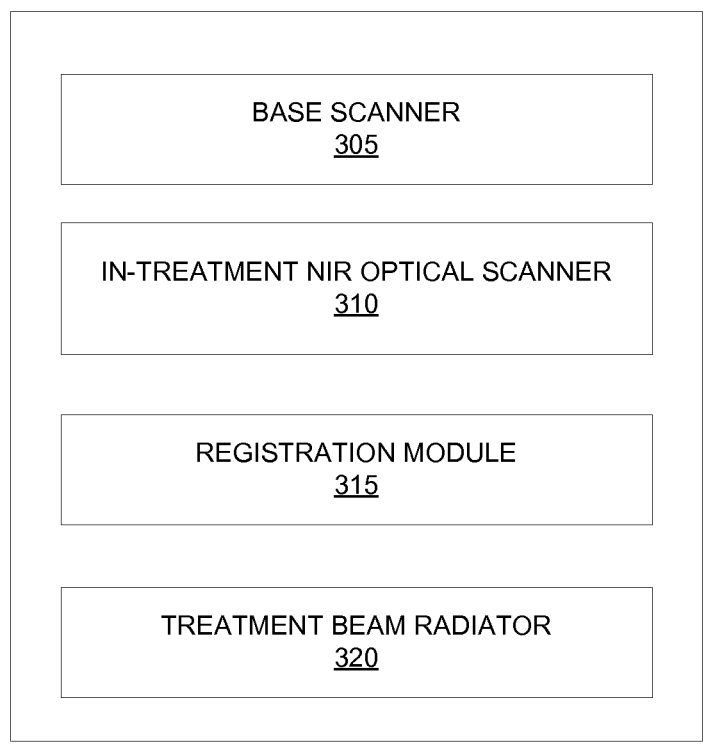
FIG. 3B is a block diagram of a treatment system configured for providing treatment of a patient including in-treatment patient localization determined through NIR imaging, in accordance with one embodiment of the present disclosure.

FIG. 3B is a block diagram of a treatment system 300B configured for providing treatment of a patient including in-treatment patient localization determined through NIR imaging, in accordance with one embodiment of the present disclosure. For instance, treatment system 300B is configurable to implement the method of FIG. 2B, and portions of FIG. 2A to provide real-time patient modeling and localization during an in-treatment procedure, in one embodiment.

As shown, treatment system 300B includes a base scanner 305 configured for performing a base scan to obtain relative 3D positioning of a surgical target within a skeletal anatomy of an object or patient. For instance, base scanner 305 is configured to determine skin characteristics at 210 of FIG. 2A, in one embodiment. Also, base scanner 305 is configured to perform the operation at 260 of FIG. 2B, in one embodiment.

System 300B also includes an in-treatment NIR optical scanner 310 configured to determine 3D positioning of the skeletal anatomy within a treatment system or environment. For instance, scanner 310 is configured to perform an in-treatment optical scan, such as, those operations outlined in 220 of FIG. 2A, and the operations outlined in 265 of FIG. 2B. In that manner, reflected, transmitted, and fluorescent signals are detectable at one or more detectors (not shown) and used for determining a model of the patient. In one embodiment, the skin characteristics are filtered using a filter (not shown) out from the detected signals to obtain a skeletal model of the patient using a modeling module (not shown).

System 300B also includes a registration model 315 that is configured for registering the 3D positioning of the skeletal anatomy obtained from the in-treatment optical scan and the 3D positioning of the skeletal anatomy determined from the base scan to determine relative positioning of the surgical target within the treatment system. System 300B also includes a treatment beam radiator 320 that is configured for exposing the surgical target to a treatment beam radiation originating from the treatment system.

Figure 3C:
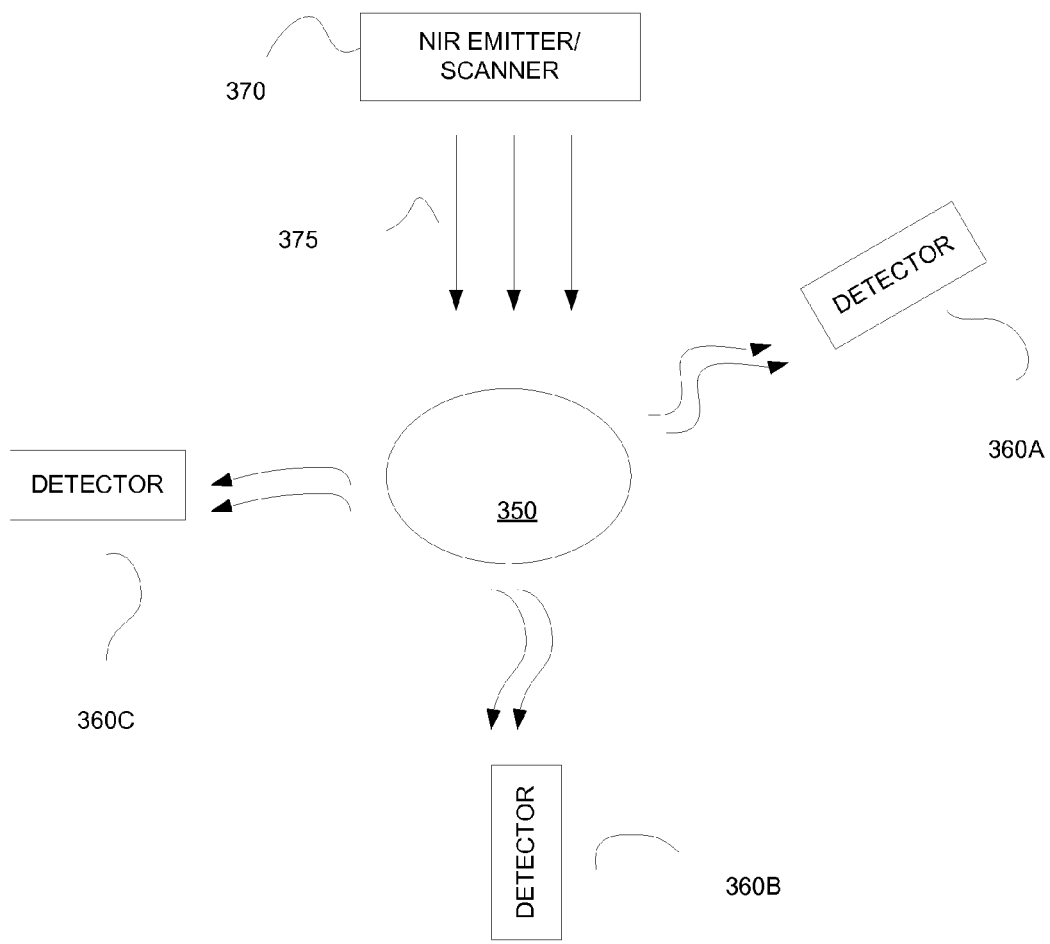
FIG. 3C is an illustration of the application of an NIR imaging system configured for providing 3D patient localization, in accordance with one embodiment of the present disclosure.

FIG. 3C is an illustration of the application of an NIR imaging system 300C configured for providing 3D patient localization, in accordance with one embodiment of the present disclosure. For instance, NIR imaging system 300C is implementable to provide pre-treatment optical scanning used for skin characterization, and in-treatment optical scanning used for determining both in-treatment patient modeling and localization.

In particular, system 300C includes an NIR apparatus as the NIR optical scanner 370 for emitting energy 375 onto an object 350 (e.g., patient). In some implementations, NIR instrumentation for NIR spectroscopy includes a source, a detector, and a dispersive element (e.g., prism or diffraction grating). This allows intensity at different wavelengths to be recorded and sampled either in reflection or transmission mode. Any source for producing NIR radiation may be used.

Detectors 360A-C are sensitive to the range of wavelengths used, and include charge-coupled device image sensors, complimentary metal-oxide-semiconductor (CMOS) based sensors, phosphorous based IR-visible converters, InGaAs photodiodes, etc., taken alone or in combination. These sensors are used to record NIR spectra obtained from reflected, fluorescent, and/or transmitted energy originating from the scanner 370. As an example, detector 360A is used to detect reflected wavelengths or energy, detector 360B is used to detect transmitted wavelengths or energy, and detector 360C is used to detect florescent energy. In embodiments, one or more detectors are use, wherein each detector is configured to detect one or more of the reflected, fluorescent, and/or transmitted energy.

Thus, according to embodiments of the present disclosure, systems and methods are described providing for patient modeling and localization using NIR imaging.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered as examples because many other architectures can be implemented to achieve the same functionality.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. These software modules may configure a computing system to perform one or more of the example embodiments disclosed herein. One or more of the software modules disclosed herein may be implemented in a cloud computing environment. Cloud computing environments may provide various services and applications via the Internet. These cloud-based services (e.g., software as a service, platform as a service, infrastructure as a service, etc.) may be accessible through a Web browser or other remote interface. Various functions described herein may be provided through a remote desktop environment or any other cloud-based computing environment.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as may be suited to the particular use contemplated.

Embodiments according to the present disclosure are thus described. While the present disclosure has been described in particular embodiments, it should be appreciated that the disclosure should not be construed as limited by such embodiments.

What is claimed is:

1. A method for treatment, comprising:
performing a base scan to obtain relative 3D positioning of a target within a skeletal anatomy of a patient;
performing an in-treatment optical scan on said patient to determine 3D positioning of said skeletal anatomy within a treatment system, wherein said in-treatment optical scan comprises a near infrared (NIR) energy source, and wherein said performing an in-treatment optical scan comprises:
  detecting a plurality of detected signals from said optical scan; and
  filtering out signaling characteristics for skin of said patient from said plurality of detected signals to obtain signals related to said skeletal anatomy and determine said 3D positioning of said skeletal anatomy; and
registering said 3D positioning of said skeletal anatomy from said in-treatment optical scan and said 3D positioning of said skeletal anatomy determined from said base scan to determine relative positioning of said target within said treatment system.

2. The method of claim 1, further comprising:
exposing said target to treatment beam radiation from said treatment system.

3. The method of claim 1, wherein said performing a base scan comprises:
performing a computed tomography (CT) scan.

4. The method of claim 1, wherein said performing a base scan comprises:
performing an magnetic resonance imaging (MRI) scan.

5. The method of claim 1, further comprising:
performing another optical scan using a source emitting NIR energy on said region of said patient, wherein said optical scan is performed over varying frequencies and intensities; and
determining said signaling characteristics for skin related to at least one of skin reflectance characteristics, skin transmittive characteristics, and a skin fluorescence characteristics, such that said signaling characteristics are filterable from said plurality of detected signals.

6. The method of claim 1, further comprising:
performing another optical scan on said patient across varying frequencies and intensity using another NIR energy source;
determining an optimal frequency and intensity combination that optimally illuminates said skeletal anatomy with minimal skin signaling characteristics; and
performing said in-treatment optical scan on said patient using said optimal frequency and intensity combination.

7. The method of claim 1, wherein said registering said 3D positioning of said skeletal anatomy further comprises:
performing a least squared comparison process to correlate said 3D positioning of said skeletal anatomy.

8. The method of claim 1, further comprising:
performing said in-treatment optical scan on said patient on a periodic basis;
updating registration of said 3D positioning of said skeletal anatomy from said in-treatment optical scan and said 3D positioning of said skeletal anatomy determined from said base scan based on a current in-treatment optical scan to determine current relative positioning of said target within said treatment system; and
aligning said target and said treatment beam radiation based on said current relative positioning to expose said target to said treatment beam radiation.

\* \* \* \* \*